United States Patent [19]

Tabei et al.

[11] Patent Number: 5,359,106
[45] Date of Patent: Oct. 25, 1994

[54] TERMINALLY REACTIVE POLYSILANE AND PROCESS FOR MAKING

[75] Inventors: Eiichi Tabei; Shigeru Mori, both of Kawasaki, Japan

[73] Assignee: Shin-Etsu Chemical Co., Ltd., Tokyo, Japan

[21] Appl. No.: 171,437

[22] Filed: Dec. 22, 1993

[30] Foreign Application Priority Data

Dec. 24, 1992 [JP] Japan .................. 4-357521

[51] Int. Cl.$^5$ .................. C07F 7/08; C07F 7/10
[52] U.S. Cl. .................. 556/413; 556/430; 549/215
[58] Field of Search .................. 556/430, 413; 549/215

[56] References Cited

U.S. PATENT DOCUMENTS

| | | | |
|---|---|---|---|
| 3,277,047 | 10/1966 | Selin | 556/430 X |
| 5,041,588 | 8/1991 | Caporiccio | 556/413 |
| 5,214,176 | 5/1993 | Soula et al. | 556/430 X |

OTHER PUBLICATIONS

Zhang et al, *J. of Polymer Science: Polymer Chem. Edition*, vol. 22, (1984), pp. 159-170.
Kumada et al, *J. of Organometallic Chemistry*, vol. 2, (1964), pp. 478-484
*J. of Polymer Science: Polymer Letters Edition*, vol. 21, (1983), pp. 819-822.
Wolff et al, *Applied Organometallic Chemistry*, (1987), vol. 1, pp. 7-14.
Ishikawa et al, *J. of Organometallic Chemistry*, vol 23, (1970), pp. 63-69.
*Chemistry & Industry*, vol. 42, No. 4, (1989) pp. 744-747.
West, *J. of Organometallic Chemistry*, vol. 300, (1986) pp. 327-346.

*Primary Examiner*—Paul F. Shaver
*Attorney, Agent, or Firm*—Birch, Stewart, Kolasch & Birch

[57] ABSTRACT

Terminally reactive polysilanes of formula (1) are novel.

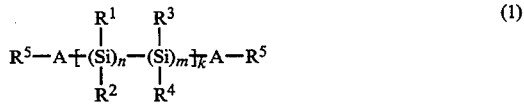

$R^1$, $R^2$, $R^3$, and $R^4$ are independently $C_{1-12}$ alkyl or aryl groups, $R^5$ is an organic group containing an alkoxysilyl, epoxy, glycidyloxy, acryl, methacryl, acetoxysilyl or amino group, A is a $C_{2-6}$ alkylene group, n, m and k are numbers in the range: $0 \leq n \leq 10$, $0 \leq m \leq 10$, $n+m \geq 10$, and $k \geq 1$. The polysilanes are prepared by effecting addition reaction between a hydro-terminated polysilane and an unsaturated group-containing reactive compound in the presence of a hydrosilylation catalyst.

7 Claims, No Drawings

TERMINALLY REACTIVE POLYSILANE AND PROCESS FOR MAKING

BACKGROUND OF THE INVENTION

1. Field of the Invention

This invention relates to terminally reactive polysilanes which are capable of accepting any desired functional group and useful as a source material for forming copolymers with other polymers. It also relates to a process for preparing the same.

2. Prior Art

Most industrial processes for preparing polysilanes utilize coupling reaction of dihalogenosilanes with alkali metals as reported in Journal of Polymer Science: Polymer Chemistry Edition, Vol. 22, 159–170 (1984), Journal of Organometallic Chemistry, Vol. 300, 327 (1986), and Journal of Polymer Science: Polymer Letter Edition, Vol. 21, 819 (1983). These processes produce polysilanes in the form of mixtures of cyclic polymers and halo- or hydrogen-terminated polymers. It is difficult to quantitatively obtain terminally modified polymers from these mixtures.

With respect to the synthesis of single end modified polysilanes, Sakurai et al. attempted living polymerization from polymers containing a disilane unit for introducing hydrogen or carboxylic acid as well as copolymerization of such polymers with polymethyl methacrylate (PMMA) as reported in Kagaku to Kogyo (Chemistry & Industry), Vol. 42, No. 4, 744. This attempt, however, has several industrial problems including limited type of substituents and limited availability of monomers.

Exemplary synthesis of terminally reactive polysilanes is reported in Journal of Organometallic Chemistry, Vol. 2, 478–484 (1964) and Journal of Organometallic Chemistry, Vol. 23, 63–69 (1970). More specifically, chloro-terminated oligosilanes can be prepared by reacting permethyloligosilanes with acetyl chloride in the presence of aluminum chloride. Also chloro-terminated oligosilanes can be prepared by reacting phenyl-terminated oligosilanes with hydrogen chloride or chlorosilane in the presence of aluminum chloride. These chloro-terminated oligosilanes, however, have a low degree of polymerization.

Focusing on the reaction that on exposure to ultraviolet (UV) radiation, polysilanes decompose and convert to those of a lower molecular weight while yielding highly reactive silylene and silyl radicals as reported in Applied Organometallic Chemistry, Vol. 1, 7–14 (1987), the inventors found that when high-molecular weight polysilanes are photodecomposed by selecting a chlorinated hydrocarbon as a solvent prone to chlorine withdrawal and exposing the polysilanes to UV radiation in the chlorinated hydrocarbon, silyl radicals generate and then form chloro-terminated polysilanes having a high degree of polymerization (see Japanese Patent Application No. 30103/1992 or U.S. Ser. No. 08/006,487).

We also found that by reacting chloro-terminated polysilanes with $LiAlH_4$ for reduction, there are obtained hydro-terminated polysilanes having a high degree of polymerization, which have never been reported of synthesis (see Japanese Patent Application No. 223372/1992 or U.S. Ser. No. 08/096,259).

The term chloro- or hydro-terminated means that the polysilane is terminated with chlorine or hydrogen at both ends of its molecular chain unless otherwise stated.

SUMMARY OF THE INVENTION

An object of the present invention is to provide a simple process of preparing a terminally reactive polysilane from the above-synthesized hydro-terminated polysilane. Another object of the present invention is provide a terminally reactive polysilane which have a high degree of polymerization, can accept any desired functional group and are useful as a source material for forming copolymers with other polymers or crosslinked molecules.

We have found that a novel terminally reactive polysilane of formula (1) having a high degree of polymerization can be prepared by effecting addition reaction between a hydro-terminated polysilane of formula (2) and an unsaturated group-containing reactive compound of formula (3) in the presence of a hydrosilylation catalyst. The reaction scheme is shown below.

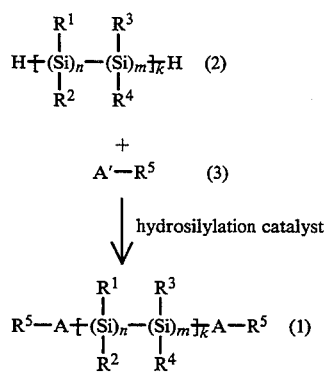

$R^1$, $R^2$, $R^3$, and $R^4$ are independently selected from alkyl groups having 1 to 12 carbon atoms and aryl groups, $R^5$ is an organic group containing at least one member selected from the group consisting of alkoxysilyl, epoxy, glycidyloxy, acryl, methacryl, acetoxysilyl, and amino groups, A is an alkylene group having 2 to 6 carbon atoms, A' is an alkenyl group having 2 to 6 carbon atoms, letters n, m and k are numbers in the range: $0 \leq n \leq 10$, $0 \leq m 23 \; 10$, $n+m \geq 10$, and $k \geq 1$.

Since the novel polysilane of formula (1) has an alkoxy, epoxy, (meth)acryl, acetoxy or amino group at either end, it can form copolymers with other polymers having a functional group such as hydroxy and (meth)acryl groups. The polysilane itself and its copolymers are useful as optical functional materials. Having such a reactive group, the polysilane can be crosslinked to form a film which is improved in durability.

Accordingly, the present invention provides a novel terminally reactive polysilane of formula (1) and a process for preparing such a polysilane by effecting addition reaction between a hydro-terminated polysilane of formula (2) and an unsaturated group-containing reactive compound of formula (3) in the presence of a hydrosilylation catalyst.

DETAILED DESCRIPTION OF THE INVENTION

The terminally reactive polysilane of the present invention is represented by formula (1).

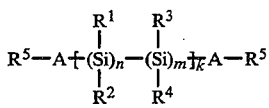

$$R^5-A+(Si)_n-(Si)_m\}_k A-R^5 \quad (1)$$

with substituents $R^1, R^2$ (top/bottom of first Si) and $R^3, R^4$ (top/bottom of second Si).

$R^1$, $R^2$, $R^3$, and $R^4$, which may be identical or different, are alkyl groups having 1 to 12 carbon atoms, preferably 1 to 8 carbon atoms or aryl groups having up to 12 carbon atoms, preferably up to 8 carbon atoms. Exemplary alkyl groups are lower alkyl groups such as methyl, ethyl and propyl groups. Exemplary aryl groups are phenyl, tolyl and styryl groups. $R^5$ is an organic group containing a lower alkoxysilyl, epoxy, glycidyloxy, acryl, methacryl, acetoxysilyl or amino group. A is an alkylene group having 2 to 6 carbon atoms, for example, ethylene and trimethylene groups. Letters n, m and k are numbers in the range: $0 \leq n \leq 10$, $0 \leq m \leq 10$, $10 \leq n+m$, and $1 \leq k$. For polysilanes to exhibit photoconductive properties, k is preferably at least 5, especially at least 10.

The terminally reactive polysilane of formula (1) is prepared by first synthesizing a hydro-terminated polysilane from a chloro-terminated polysilane.

The chloro-terminated polysilane can be prepared by the method we previously proposed in Japanese Patent Application No. 101804/1992 or U.S. Ser. No. 08/006,487.

More particularly, a polysilane of formula (4) shown below is prepared by effecting coupling reaction of a dichlorosilane with an alkali metal such as sodium. The resulting polysilane preferably has a number average molecular weight (Mn) of at least 1,000. Next, the polysilane is dissolved in a chlorinated hydrocarbon, such as dichloromethane, chloroform, carbon tetrachloride, 1,2-dichloroethane, 1,1,2-trichloroethane and 1,1,2,2-tetrachloroethane to form a solution at a concentration of about 1 to 20% by weight. The polysilane solution is irradiated with UV radiation in an inert gas atmosphere such as nitrogen gas and argon gas. After exposure to a predetermined dose of UV, the reaction solution is concentrated to $\frac{1}{2}$ to 1/5 in volume. By adding hexane to the concentrate in an amount of about 150 grams per 10 grams of the polysilane, the chloro-terminated polysilane is caused to form a precipitate. Through filtration and drying, the chloro-terminated polysilane of formula (5) having a number average molecular weight (Mn) of at least 1,000 is obtained as white powder.

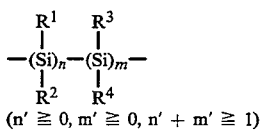

$$-(Si)_{n'}-(Si)_{m'}- \quad (4)$$
$$(n' \geq 0, m' \geq 0, n' + m' \geq 1)$$

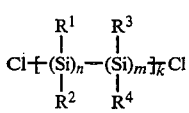

$$Cl+(Si)_n-(Si)_m\}_k Cl \quad (5)$$

The chloro-terminated polysilane of formula (5) is dissolved in a solvent such as tetrahydrofuran (THF) preferably in a concentration of about 5 to 50% by weight, more preferably about 10 to 30% by weight. With this solution kept in an inert gas atmosphere such as nitrogen and argon gas, the chloro-terminated polysilane is reacted with LiAlH$_4$ preferably in an amount of 0.25 to 2 mol, especially 1 to 2 mol of LiAlH$_4$ per mol of chlorine, thereby reducing the chloro-terminated polysilane. After deactivation of the unreacted LiAlH$_4$ with alcohol and several times of water washing, the organic layer is collected, dried, and concentrated, obtaining a hydro-terminated polysilane of formula (2) as a white powder. The reaction temperature used herein is from room temperature to the reflux temperature of the solvent (e.g., 65° C. for THF) and the reaction time is generally about 1 to 4 hours.

The terminally reactive polysilane of formula (1) is synthesized from the hydro-terminated polysilane as a source. First the hydro-terminated polysilane of formula (2) is dissolved in a solvent. The polysilane-soluble solvents which can be used herein include tetrahydrofuran (THF), toluene and xylene. Both the polysilanes and solvents may be used alone or in admixture of two or more. The solution preferably has a concentration of about 1 to 40% by weight, more preferably about 5 to 20% by weight.

Next, a hydrosilylation catalyst is added to the solution. The hydrosilylation catalyst includes rhodium complexes such as (Ph$_3$P)$_3$RhCl wherein Ph is phenyl and platinum complexes such as chloroplatinic acid, with the rhodium complexes being preferred. The amount of the hydrosilylation catalyst added is a catalytic amount, preferably 0.001 to 5% by weight, more preferably 0.01 to 1% by weight based on the weight of the hydro-terminated polysilane.

To the solution is added an unsaturated group-containing reactive compound of formula (3):

$$A'-R^5 \quad (3)$$

wherein A' is an alkenyl group having 2 to 6 carbon atoms such as vinyl, propenyl and R$^5$ is as defined above.

Examples of the unsaturated group-containing reactive compound include allyl glycidyl ether and trimethoxyvinylsilane. Preferably the amount of the formula (3) compound added is at least the theoretical amount relative to the hydro-terminated polysilane. The solution is agitated, preferably at 50° to 150° C. for about 1 to 4 hours.

After the completion of reaction, the reaction solution is treated with activated carbon and then concentrated. The concentrate is dissolved in an organic solvent whereupon the reaction product is re-precipitated therefrom. On filtration and drying, a terminally reactive polysilane of formula (1) is obtained as a white powder.

The thus obtained polysilane of formula (1) is highly reactive due to the presence of a reactive group at either end and is useful as a component which is copolymerizable with other polymers or convertible into crosslinked polymers.

EXAMPLE

Examples of the present invention are given below by way of illustration and not by way of limitation. All parts and percents are by weight. Mn and Mw are number and weight average molecular weights, respectively, and Ph is phenyl.

Exemplary preparation of chloro- and hydro-terminated polysilanes is first described.

Preparation Examples 1-5

Methylphenylpolysilane having Mn=24,000 and Mw/Mn=3.32 was previously prepared by coupling reaction of methylphenyldichlorosilane with sodium. 7.0 grams of the methylphenyl-polysilane was dissolved in 133 grams of carbon tetrachloride in a concentration of 5%. In a nitrogen gas atmosphere, a Pyrex ® reaction tube with a diameter of 15 mm was filled with the polysilane solution, closed with a plug, and exposure to UV radiation (312 nm) in a dose of 1 J/cm$^2$ using a high-pressure mercury lamp. The reaction solution was concentrated to about 50 grams. Addition of 100 grams of hexane to the solution caused precipitation of a chloro-terminated polysilane. It was isolated by filtration and dried, obtaining a white powder (Preparation Example 1).

The procedure of Preparation Example 1 was repeated except that the UV dose was changed to 2, 3, 5 and 10 J/cm$^2$, yielding white powders (Preparation Examples 2-5).

Table 1 reports the Mn (based on polystyrene), Mw/Mn and yields of these white powders. Their chlorine contents as measured by titration are also reported together with the theoretical values.

TABLE 1

| No. | UV dose (J/cm$^2$) | Chloro-terminated polysilane | | | | |
|---|---|---|---|---|---|---|
| | | Mn | Mw/Mn | Yield (%) | Cl (%) Found | Cl (%) Calc. |
| 1 | 1 | 15,970 | 2.34 | 77 | 0.45 | 0.45 |
| 2 | 2 | 12,220 | 1.94 | 65 | 0.54 | 0.58 |
| 3 | 3 | 11,980 | 1.93 | 63 | 0.58 | 0.59 |
| 4 | 5 | 8,300 | 1.70 | 60 | 0.84 | 0.86 |
| 5 | 10 | 4,600 | 1.47 | 52 | 1.49 | 1.53 |

Preparation Example 6

In a nitrogen gas atmosphere, 5.5 grams of chloro-terminated methylphenylpolysilane (Mn=5,500, Mw/Mn=1.90) was dissolved in 50 grams of THF, and 0.15 grams of LiAlH$_4$ was added to the solution. Agitation was continued for 4 hours. At the end of reaction, 5 grams of methanol was added to the reaction mixture, which was washed with 100 grams of water three times. The organic layer was dried overnight over calcium chloride. After the desiccant was filtered off, the solution was concentrated, yielding 3.5 grams of a hydro-terminated methylphenylpolysilane as white powder.

Preparation Example 7

In a nitrogen gas atmosphere, 20.0 grams of chloro-terminated methylphenylpolysilane (Mn =7,500, Mw/Mn=2.0) was dissolved in 200 grams of THF, and 0.5 grams of LiAlH$_4$ was added to the solution. Agitation was continued for 4 hours. At the end of reaction, 20 grams of methanol was added to the reaction mixture, which was washed with 200 grams of water three times. The organic layer was dried overnight over calcium chloride. After the desiccant was filtered off, the solution was concentrated, yielding 15.8 grams of a hydro-terminated methylphenylpolysilane as white powder.

Example 1

In 20 grams of toluene was dissolved 0.5 grams of hydro-terminated methylphenylpolysilane (Mn=5,700, Mw/Mn=1.68) and then added 3 mg of [(Ph$_3$P)$_3$RhCl]. The solution was heated to a temperature of 110° C., 0.5 grams of allyl glycidyl ether was added dropwise thereto, and the solution was agitated at 110° C. for 2 hours. After the completion of reaction, the reaction solution was treated with activated carbon and concentrated. The concentrate was dissolved in 100 ml of toluene, and 20 ml of methanol was slowly added to the solution for re-precipitation. After filtration and drying, 0.35 grams of a white powder was obtained.

Measurements of this white powder are shown below.

Yield: 70% Mn: 6,100 (calculated as polystyrene) Mw/Mn: 1.90 IR analysis: 2096 cm$^{-1}$(Si—H) peak disappeared 2926 cm$^{-1}$ (CH$_2$ antisymmetric stretch) peak 2866 cm$^{-1}$ (CH stretch) peak 1263 cm$^{-1}$ (C—O—C antisymmetric stretch) peak Proton-NMR (in C$_6$D$_6$): −0.8 to 0.7 ppm (SiCH$_3$) 1.5 ppm (CH$_2$) 2.0 to 3.0 ppm (C$_2$H$_3$O) 3.0 to 3.6 ppm (CH$_2$O) 6.3 to 7.8 ppm (Ph)

These measurements imply that the white powder is a terminally glycidyloxypropyl-terminated methylphenylpolysilane.

Example 2

In 20 grams of toluene was dissolved 3.0 grams of hydro-terminated methylphenylpolysilane (Mn=8,000, Mw/Mn=1.5) and then added 3 mg of [(Ph$_3$P)$_3$RhCl]. The solution was heated to a temperature of 110° C., 1.5 grams of trimethoxyvinylsilane was added dropwise thereto, and the solution was agitated at 110° C. for 4 hours. After the completion of reaction, the reaction solution was treated with activated carbon and concentrated. The concentrate was dissolved in 10 ml of toluene, and 60 ml of hexane was slowly added to the solution for re-precipitation. After filtration and drying, 2.16 grams of a white powder was obtained.

Measurements of this white powder are shown below.

Yield: 72% Mn: 8,400 (calculated as polystyrene) Mw/Mn: 1.75 IR analysis: 2096 cm$^{-1}$ (Si—H) peak disappeared 2926 cm$^{-1}$ (CH$_2$ antisymmetric stretch ) peak 2866 cm$^{-1}$ (CH stretch) peak Proton-NMR (in C$_6$D$_6$): −0.8 to 0.7 ppm (SiCH$_3$) 1.5 ppm (CH$_2$) 6.3 to 7.8 ppm (Ph)

These measurements imply that the white powder is a terminally trimethoxysilylethyl-terminated methylphenylpolysilane.

According to the present invention, terminally reactive polysilanes having a high degree of polymerization can be synthesized in a simple manner. They allow various functional groups to be introduced therein and are useful source materials for forming copolymers with other polymers.

Although some preferred embodiments have been described, many modifications an variations may be made thereto in the light of the above teachings. It is therefore to be understood that within the scope of the appended claims, the invention may be practiced otherwise than as specifically described.

We claim:

1. A terminally reactive polysilane of the formula:

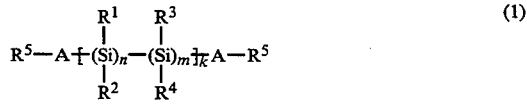

wherein $R^1$, $R^2$, $R^3$, and $R^4$ are independently selected from alkyl groups having 1 to 12 carbon atoms and aryl groups, $R^5$ is an organic group containing at least one member selected from the group consisting of alkoxysilyl, epoxy, glycidyloxy, acryl, methacryl, acetoxysilyl, and amino groups, A is an alkylene group having 2 to 6 carbon atoms, letters n, m and k are numbers in the range: $0 \leq n \leq 10$, $0 \leq m \leq 10$, $n+m \geq 10$, and $k \geq 1$.

2. A process for preparing a terminally reactive polysilane of the following formula (1):

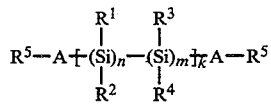  (1)

wherein $R^1$, $R^2$, $R^3$, and $R^4$ are independently selected from alkyl groups having 1 to 12 carbon atoms and aryl groups, $R^5$ is an organic group containing at least one member selected from the group consisting of alkoxysilyl, epoxy, glycidyloxy, acryl, methacryl, acetoxysilyl, and amino groups, A is an alkylene group having 2 to 6 carbon atoms, letters n, m and k are numbers in the range: $0 \leq n \leq 10$, $0 \leq m \leq 10$, $n+m \geq 10$ and $k \geq 1$, said process comprising the step of:

effecting addition reaction between a hydro-terminated polysilane of the following formula (2):

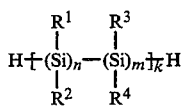  (2)

wherein $R^1$, $R^2$, $R^3$, $R^4$, n, m, and k are as defined above and an unsaturated group-containing reactive compound of the following formula (3):

  (3)

wherein A' is an alkenyl group having 2 to 6 carbon atoms and $R^5$ is as defined above in the presence of a hydrosilylation catalyst.

3. The polysilane of claim 1, wherein $R^1$, $R^2$, $R^3$ and $R^4$ are independently selected from the group consisting of methyl, ethyl, propyl, phenyl, tolyl and styryl groups.

4. The polysilane of claim 1, wherein the letter k is at least 10.

5. The process of claim 2, wherein $R^1$, $R^2$, $R^3$, and $R^4$ are independently selected from the group consisting of methyl, ethyl, propyl, phenyl, tolyl and styryl groups.

6. The process of claim 2, wherein the letter k is at least 10.

7. The process of claim 2, wherein the hydrosilylation catalyst is a rhodium complex represented by the formula $(Ph_3P)_3RhCl$, wherein Ph represents a phenyl group.

* * * * *